US008852765B2

(12) United States Patent
Hashimoto et al.

(10) Patent No.: US 8,852,765 B2
(45) Date of Patent: Oct. 7, 2014

(54) MICROBIAL FUEL CELL

(75) Inventors: Kazuhito Hashimoto, Tokyo (JP); Ryuhei Nakamura, Tokyo (JP); Fumiyoshi Kai, Tokyo (JP); Kazuya Watanabe, Chofu (JP); Soichiro Kato, Tokyo (JP)

(73) Assignees: Japan Science and Technology Agency, Saitama (JP); The University of Tokyo, Tokyo (JP)

( * ) Notice: Subject to any disclaimer, the term of this patent is extended or adjusted under 35 U.S.C. 154(b) by 12 days.

(21) Appl. No.: 12/934,876

(22) PCT Filed: Mar. 27, 2009

(86) PCT No.: PCT/JP2009/056385
§ 371 (c)(1),
(2), (4) Date: Oct. 29, 2010

(87) PCT Pub. No.: WO2009/119846
PCT Pub. Date: Oct. 1, 2009

(65) Prior Publication Data
US 2011/0236725 A1 Sep. 29, 2011

(30) Foreign Application Priority Data

Mar. 28, 2008 (JP) ................................. 2008-086195
Sep. 26, 2008 (JP) ................................. 2008-249178

(51) Int. Cl.
*H01M 8/16* (2006.01)
*C12N 1/20* (2006.01)
*H01M 4/86* (2006.01)
*H01M 4/90* (2006.01)
*C12P 3/00* (2006.01)
*C12P 1/04* (2006.01)

(52) U.S. Cl.
CPC .............. *C12N 1/20* (2013.01); *H01M 4/8673* (2013.01); *H01M 4/90* (2013.01); *C12P 3/00* (2013.01); *H01M 8/16* (2013.01); *H01M 4/8605* (2013.01); *Y02E 60/527* (2013.01); *C12P 1/04* (2013.01)

USPC .............................................. 429/2; 429/401

(58) Field of Classification Search
USPC ...................................................... 429/2, 401
See application file for complete search history.

(56) References Cited

U.S. PATENT DOCUMENTS

2005/0013759 A1* 1/2005 Grow ........................... 423/263
2007/0259217 A1 11/2007 Logan (Continued)

FOREIGN PATENT DOCUMENTS

EP          1 947 716 A1    7/2008
JP          2006-081963 A   3/2006
WO          2007/037228     4/2007

OTHER PUBLICATIONS

Logan et al. "Electricity-producing bacterial communities in microbial fuel cells", Trends in Microbiology; vol. 14 Issue 12, Dec. 2006, pp. 512-518.*

(Continued)

*Primary Examiner* — Patrick Ryan
*Assistant Examiner* — Lucas J O'Donnell
(74) *Attorney, Agent, or Firm* — Duane Morris LLP; J. Rodman Steele, Jr.; Gregory M. Lefkowitz

(57) ABSTRACT

It is an object of the present invention to provide a microbial fuel cell capable of increasing a current density without employing a mediator. The microbial fuel cell 1 includes a 3-dimensionally structured agglomerate formed from conductive fine particles 2 and microorganisms 3. In the agglomerate 4, the conductive fine particles 2 disperse among pieces of *Shewanella* 3 and the conductive fine particles 2 are coupled to one another to hold *Shewanella* 3, thus forming the 3-dimensional structure as a whole. Accordingly, with respect to *Shewanella* 3, conductive fine particles 2 hold *Shewanella* 3a on a surface of an electrode 103 and even *Shewanella* 3b positioned vertically away from the surface of the electrode 103. Hence, it becomes possible that more pieces of *Shewanella* 3 are allowed to transfer electrons.

17 Claims, 9 Drawing Sheets

(56) References Cited

U.S. PATENT DOCUMENTS

2008/0261083 A1* 10/2008 Rinzler et al. .................... 429/2
2009/0169924 A1* 7/2009 Ringeisen et al. ................ 429/2
2009/0297890 A1* 12/2009 Shimomura et al. ............. 429/2

OTHER PUBLICATIONS

Gorby et al., "Electrically conductive bacterial nanowires produced by Shewanella oneidensis strain MR-1 and other microorganisms", Proceedings of the National Academy of Sciences (PNAS), Jul. 25, 2006; vol. 103, No. 30.*

Bretschger, O. et al. (2007) "Current Production and Metal Oxide Reduction by Schewanella oneidensis MR-1 Wild Type and Mutants," Applied and Environmental Microbiology, 73(21): 7003-7012.

Cho, E.J. et al. (2007) "Optimization of the biological component of a bioelectrochemical cell," Bioelectrochemistry, 70: 165-172.

Eggleston, C.M. et al. (2008) "Binding and direct electrochemistry of OmcA, an outer-membrane cytochrome from an iron reducing bacterium, with oxide electrodes: A candidate biofuel cell system," Inorganica Chimica Acta, 361: 769-777.

Gralnick, J.A. et al. (2007) "Extracellular respiration," Molecular Microbiology, 65(1): 1-11.

He, Z. et al. (2005) "Electricity Generation from Artificial Wastewater Using an Upflow Microbial Fuel Cell," Environ. Sci. Technol., 39: 5262-5267.

He, Z. et al. (2006) "An Upflow Microbial Fuel Cell with an Interior Cathode: Assessment of the Internal Resistance by Impedance Spectroscopy," Environ. Sci. Technol., 40: 5212-5217.

Hernandez, M.E. et al. (2001) "Extracellular electron transfer," Cellular and Molecular Life Sciences, 58: 1562-1571.

Ishii, S. et al. (2008) "Electron Transfer by Microorganisms in a Microbial Fuel Cell," Bulletin of Japanese Society of Microbial Ecology, 23(2): 58-69.

Kim, H.J. et al. (1999) "A Microbial Fuel Cell Type Lactate Biosensor Using a Metal-Reducing Bacterium, Shewanella putrefaciens," J. Microbiol. Biotechnol., 9(3): 365-367.

Lovley, D.R. (2006) "Bug juice: harvesting electricity with microorganisms," Microbiology, 4: 497-508.

Manohar, A.K. et al. (2008) "The polarization behavior of the anode in a microbial fuel cell," Electrochimica Acta, 53: 3508-3513.

Nakamura, R. et al. (2007) "Direct Electron Transfer Reaction between Microorganism and Metallic Oxide on Semiconductor Interface," Proceedings of the 26th Solid-Surface Photochemistry Symposium: 68-69.

Rabaey, K. et al. (2005) "Tubular Microbial Fuel Cells for Efficient Electricity Generation," Environ. Sci. Technol., 39: 8077-8082.

Sell, D. et al. (1989) "Use of an oxygen gas diffusion cathode and a three-dimensional packed bed anode in a bioelectrochemical fuel cell," Applied Microbiology Biotechnology, 31: 211-213.

D. Sell, et al., Use of an Oxygen Gas Diffusion Cathode and a Three-Dimensional Packed Bed Anode in a Bioelectrochemical Fuel Cell, Applied Microbiology and Biotechnology, 1989, 31:211-213, Springer-Verlag, Germany.

* cited by examiner

MICROBIAL FUEL CELL

CROSS-REFERENCE TO RELATED APPLICATIONS

This application is a §371 national stage entry of International Application No. PCT/JP2009/056385, filed Mar. 27, 2009, and Japanese Patent Application No. 2008-086195, filed Mar. 28, 2008, and Japanese Patent Application No. 2008-249178, filed Sep. 26, 2008, the entireties of which are hereby incorporated by reference.

TECHNICAL FIELD

The present invention relates to a microbial fuel cell.

BACKGROUND ART

A microbial fuel cell is equipped with a pair of electrodes, an external circuit for electrically connecting the electrodes, and a separating film for separating the pair of the electrodes. Microorganisms with an extracellular electron transfer capability, such as *Shewanella* or the like are held on one electrode. Here, the extracellular electron transfer capability means the capability to obtain biogenic electric energy and at the same time transfer electrons to electron accepters by utilizing metallic ions and their oxidative products as the electron accepters to reduce the ions and the products (see nonpatent document 1). The forgoing extracellular electron transfer capability is found in part of bacteria acting as microorganisms. That is, a specific electron transfer mechanism that discharges electrons to the outsides of microorganisms via cytochrome localized in a cell membrane is found in part of bacteria, such as a *Shewanella* group (hereunder, simply referred to as *Shewanella*) such as *Shewanella loihica* and *Shewanella oneidensis*, a *Geobacter* group, a *Rhodoferax* group, a *Pseudomonas* group or the like (see nonpatent documents 2, 3, 4).

The microbial fuel cell thus structured is a device in which microorganisms transfer electrons to the above one electrode, thereby producing electric energy. As fuel for producing electric energy, a regenerable biomass and organic pollutants contained in human sewage or the like can be utilized and hence the microbial fuel cell has recently received widespread attention as a sustainable energy source. Besides, there also exist microorganisms with a capability to reduce and fixate a metallic element, which has been noted as means for sewage treatment and environmental purification, too. The microbial fuel cell falls into the two general classifications which are a system for employing a single kind of microorganism, and a mixed bacterial culture system for directly employing a microbial group living in sewage or the like (e.g., see patent document 1).

*Shewanella* is a microorganism most extensively employed in the former system.

Patent document 1: Japanese unexamined patent application publication No. 2006-81963.

Nonpatent document 1=Lovely D. R.; Nat. Rev. Microbiol., 2006, 4, 497-508

Nonpatent document 2: Gralnick, J. A.; Newman, D. K.; Molecul. Microbiol. 2007, 65, 1-11

Nonpatent document 3: Hernandez, M. E.; Newman, D. K.; Cell. Mol. Life Sci. 2001. 58, 1562-1571

Nonpatent document 4: Journal of Japanese Society of Microbial Ecology (2008) Vol. 23, No. 2, P. 58

DISCLOSURE OF THE INVENTION

Problem to be Solved by the Invention

Under existing condition, however, in the traditional microbial fuel cell described in the above patent document 1 or the like, as compared to the existing chemical fuel cell which employs the existing platinum as catalyst, its current density is extremely low and has become a problem, thus making the traditional microbial fuel cell off from a stage of practical use. For the last few years, the current density has been continuously improved. As compared to a chemical fuel cell such as a hydrogen fuel cell, however, it is impossible for the microbial fuel cell to advance to its practical use unless its current density is improved by at least on the order of several more digits. For the purpose of increasing the current density, studies have been carried out to add a mediator for transferring electrons. And, as the mediator to be added, a quinine derivative such as anthraqunore-2,6-disulphonate (AQDS) or the like is known. The mediator itself, however, is expensive and many of them are noxious, accompanied by the problem that the size of the microbial fuel cell tends to be large as a whole.

Therefore, with the view of the problems described above, it is an object of the present invention to provide a microbial fuel cell capable of increasing its current density without employing a mediator.

Means for Solving the Problem

In order to achieve the above object, a first aspect of the present invention provides a microbial fuel cell equipped with a pair of electrodes and an external circuit for electrically connecting the pair of the electrodes. In the microbial fuel cell, on a negative electrode, being one electrode of the electrodes, a 3-dimensionally structured agglomerate is formed in a solution containing conductive fine particles and microorganisms with an extracellular electron transfer capability, and the conductive fine particles transfer electrons from the microorganisms to the negative electrode.

A second aspect of the present invention is a microbial fuel cell in which the conductive fine particles are dispersed among the microorganisms and are coupled to one another to hold the microorganisms.

A third aspect of the present invention is a microbial fuel cell in which the conductive fine particles contain ferric oxide.

A fourth aspect of the present invention is a microbial fuel cell in which the conductive fine particles contain $\alpha$-$Fe_2O_3$, $\alpha$-FeOOH, $\gamma$-$Fe_2O_3$, $\epsilon$-$Fe_2O_3$ or $Fe_3O_4$.

A fifth aspect of the present invention is a microbial fuel cell in which the conductive fine particles contain ferric sulfide.

A sixth aspect of the present invention is a microbial fuel cell in which the conductive fine particles are obtained by biosynthesis of microorganisms in an environment where iron ions and sulfide ions are present.

A seventh aspect of the present invention is a microbial fuel cell in which the conductive fine particles contain manganese oxide.

An eighth aspect of the present invention is a microbial fuel cell in which the microorganisms are metal-reducing bacteria.

A ninth aspect of the present invention is a microbial fuel cell in which the metal-reducing bacteria contain bacteria of a *Shewanella* group, a *Geobacter* group, a *Rhodoferax* group or a *Pseudomonas* group.

A tenth aspect of the present invention is a microbial fuel cell in which the metal-reducing bacteria contain *Shewanella loihica* or *Shewanella oneidensis*.

Effects of the Invention

According to the microbial fuel cell of the present invention, a network made up of the conductive fine particles allows electrons to transfer from the microorganisms to the electrode, and thus, electrons can be transferred even from microorganisms suspending far away from the electrode to the electrode. Hence, its current density can be increased.

BEST MODE FOR CARRYING OUT THE INVENTION

Microorganisms according to the present invention have an extracellular electron transfer capability to discharge electrons to the organisms via cytochrome localized in a cell membrane. Electrons are transferred to an external electrode to produce a current. The present invention provides a microbial fuel cell utilizing the properties of these microorganisms.

There are a multiple of factors for determining a current generation capability in a microbial fuel cell. A specific surface area of an electrode, a device scale and a selection of an electrode material are common factors in a microbial fuel cell as well in a chemical cell, while the electron transfer from microorganisms to an electrode is unique to a microbial fuel cell, which is the most important factor above all. Nevertheless, there is little or no research paper which has studied the reaction mechanism of the electron transfer from microorganisms to an electrode and led to achievement of an increase in current density. As a reason for that, it can be pointed out that a system has been not known which was suitable to electrochemically study an electrode reaction of a living microorganism for generating a current. With the focus on this point, the present inventors accomplished the present invention as a result of performing an electrochemical study.

In addition, the following description is given with *Shewanella*, being a type of microorganism, taken as an example. *Shewanella* has an extracellular electron transfer capability to transfer electrons directly to an electrode via cytochrome localized in a cell membrane. Besides, *Shewanella* has a capability to reduce metallic ions and insoluble metallic oxide (a metal-reducing bacterium).

Figure 1:
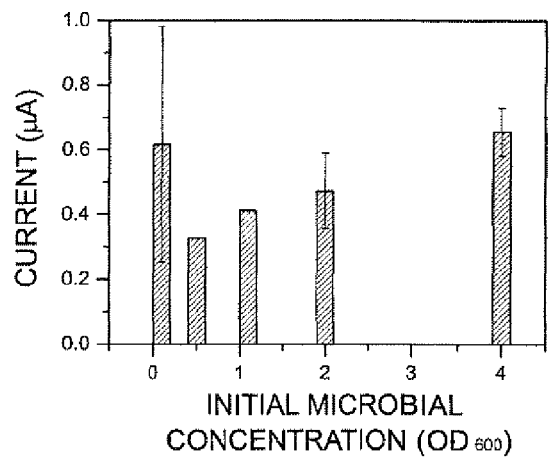
FIG. 1 is a graph illustrating a relationship between an initial microbial density ($OD_{600}$) and a steady current, in an electrochemical cell.

FIG. 1 shows a relationship between a concentration of *Shewanella* and a steady current value. The concentration of *Shewanella* was measured by a light transmission amount, which is called an OD method. In addition, OD (600 nm) means an intensity of 600 nm light when a suspending solution of microorganisms is put in a cell having a light path length 1 cm. Here, a rough indication for the number of the microorganisms is $10^{18}$ pieces/ml, when OD=1.0. As is clear from FIG. 1, the steady current value has been proved to be out of relation to the *Shewanella* concentration. A generated current has been proved to be relevant not to an amount of microorganisms but to an amount of the microorganisms existing in the vicinity of an electrode.

As a result of having studied the microbial fuel cell utilizing this *Shewanella*, electron transfer is carried out only in the *Shewanella* present in the vicinity of a surface of the electrode, while little or no electron transfer was carried out in the *Shewanella* suspended far away from the electrode and hence this *Shewanella* contributed to no current generation. Then, it was found that such a noncontributory condition of this *Shewanella* disabled a large current density to be obtained.

Figure 2A:
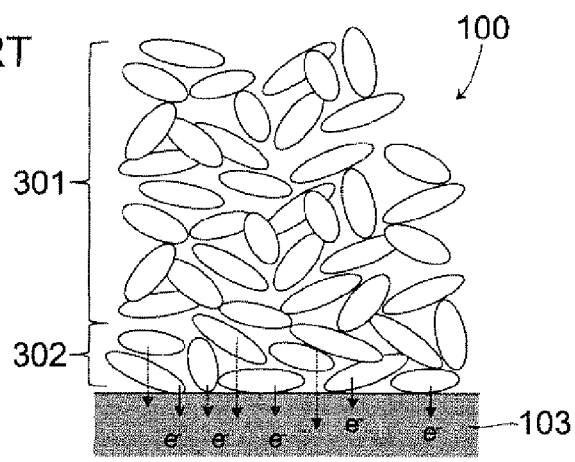
FIG. 2 is a conceptual diagram illustrating a positional relationship of microorganisms on an electrode, (a) microorganisms on the traditional electrode, (b) a model diagram of 3-dimensionally structured agglomerate formed from microorganisms and the conductive fine particles.

Specifically, as shown in FIG. 2(a), in an electrode 103 of the traditional microbial fuel cell 100, only the *Shewanella* 302 present in the vicinity of the electrode 103 carries out the electron transfer, whereas the *Shewanella* 301 suspended far away from the electrode carries out little or no electron transfer. Accordingly, if the *Shewanella* 301 suspended far away from the electrode 103 can be made to infallibly carry out the electron transfer, it is considered that a current density of a microbial fuel cell 100 can be dramatically increased as compared to the traditional one.

Then, the present inventors found out that *Shewanella* specifically adsorbed conductive fine particles and agglomerated with the conductive fine particles in a solution to form 3-dimensionally-structured agglomerate and a network made up of the conductive fine particles in the agglomerates allowed electrons to transfer from the *Shewanella* to the electrode and as a result *Shewanella* was led to have a function to enable electrons to be transferred even from the *Shewanella* suspended far away from the electrode to the electrode. Here, the agglomerate means a 3-dimensionally-structured state where the agglomerate is equipped with the *Shewanella*, being a microorganism, and the conductive fine particles and the *Shewanella* specifically adsorbed the conductive fine particles. Besides, as the conductive fine particles, a variety of matters is taken into account and fine particles of matter such as ferric oxide, manganese oxide and ferric sulfide are applicable.

Figure 2B:
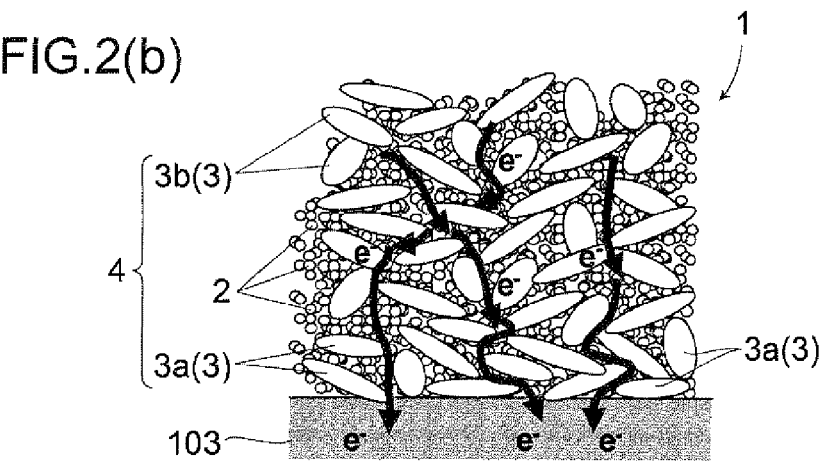

In the microbial fuel cell 1 according to the present example, as shown in FIG. 2(*b*), on a surface of the electrode 103, the 3-dimensionally-structured agglomerate is formed from the conductive fine particles 2 and *Shewanella* 3. In this agglomerate 4, the conductive fine particles 2 disperse among respective pieces of the *Shewanella* 3, and the conductive fine particles 2 are coupled to one another to hold the *Shewanella* 3, thus forming the 3-dimensional structure as a whole. Accordingly, the conductive fine particles 2 can hold the *Shewanella* 3 including *Shewanella* 3*a* on the surface of the electrode 103 and even *Shewanella* 3*b* positioned in a vertical direction a distance away from the surface of the electrode 103. As described above, in the microbial fuel cell 1 according to the present invention, the *Shewanella* 3 is allowed to be held by the conductive fine particles 2, extensively, i.e., particularly over a range of zone extending vertically away from the surface of the electrode 103. Hence, more pieces of the *Shewanella* 3 are allowed to transfer electrons. Besides, the *Shewanella* 3 is held by means of the conductive fine particles 2 and therefore electrons e⁻ can be infallibly transferred to the electrode 103 even from positions away from the electrode 103. Accordingly, in the microbial fuel cell 1 according to the present example, its current density can be dramatically increased.

As described above, in the microbial fuel cell in which the conductive fine particles represented by ferric oxide and *Shewanella* form the 3-dimensionally-structured agglomerate, as compared to the traditional microbial fuel cell where no conductive fine particle exists, the current density can be dramatically increased by *Shewanella*. Here, as a conductive fine particle, metallic oxide, e.g., can be recommended. In this case, as metallic oxide, ferric oxide and manganese oxide, e.g., can be applicable. In this case, as ferric oxide, $\alpha\text{-Fe}_2O_3$, $\alpha\text{-FeOOH}$, $\gamma\text{-Fe}_2O_3$, $\epsilon\text{-Fe}_2O_3$ or $Fe_3O_4$ are applicable.

Furthermore, as a conductive fine particle, ferric sulfide can be employed. In this case, ferric sulfide can be obtained by biosynthesis caused by a reduction action between ferric ions of microorganisms and sulfide ions thereof in an environment where ferric ions and sulfide ions are present.

Further, in terms of electric characteristics, as conductive fine particles, a semiconductor and a metal are recommended. In addition, $\alpha\text{-Fe}_2O_3$, $\alpha\text{-FeOOH}$, $\gamma\text{-Fe}_2O_3$, $\epsilon\text{-Fe}_2O_3$, which are described above, are semiconductors, while $Fe_3O_4$ and manganese oxide are metals.

In the microbial fuel cell employed in the present invention, between pieces of *Shewanella* or on a surface of *Shewanella*, metallic oxide acting as a conductive fine particle, nanosized ferric oxide fine particles, e.g., exist to form 3-dimensionally-structured agglomerate as a whole. A microbial fuel cell, in which metallic oxide exists between pieces of *Shewanella* or on the surface of *Shewanella* and 3-dimensionally-structured agglomerate are formed, has a generated current value increased by fifty or more times as large as that of the traditional microbial fuel cell without metallic oxide between pieces of *Shewanella* or on the surface of *Shewanella* and the 3-dimensional agglomerate, thus dramatically improving efficiency. Furthermore, the microbial fuel cell according to the present invention dispenses with a mediator or the like which has been traditionally employed, e.g., a mediator made of a quinone derivative or the like, thus permitting an inexpensive and highly safe fuel cell to be obtained.

As for a mechanism for increasing a current density, by adding $\alpha\text{-Fe}_2O_3$ fine particles, (1) an amount of current generated from each pieces of *Shewanella* has increased,
(2) the transfer and dispersion of *Shewanella* to the electrode has been accelerated and
(3) $\alpha\text{-Fe}_2O_3$ fine particles spontaneously agglomerated functions as a long-distance electron transferring material.

Thus three possibilities are estimated. As for the item (1), even when the same $\alpha\text{-Fe}_2O_3$ fine particles exist, a generated current value on an $\alpha\text{-Fe}_2O_3$ thin-film electrode where no 3-dimensional structure of $\alpha\text{-Fe}_2O_3$/*Shewanella* is formed was much smaller as compared to the generated current value in the case where the $\alpha\text{-Fe}_2O_3$ fine particles were added into a cell for suspending microorganisms and fine particles existing in a solution. This fact indicates that the observed dramatic increase in current density is unaccountable only by an increase in generated current value of *Shewanella*.

Furthermore, as for the item (2), with regard to the possibility that the transfer and dispersion of *Shewanella* to an ITO electrode acting as a negative electrode were accelerated by adding the $\alpha\text{-Fe}_2O_3$ fine particles, from an aspect of the ITO (indium T in Oxide; indium tin oxide) electrode after current measurement, *Shewanella* has been observed to form a robust and bulky biofilm on the ITO electrode in the presence of the $\alpha\text{-Fe}_2O_3$ fine particles as compared to the absence thereof. From this phenomenon, it is concluded that there is little or no possibility that the transfer of *Shewanella* to the ITO electrode is accelerated in the presence of the $\alpha\text{-Fe}_2O_3$ fine particles. In addition, the negative electrode is schemed so that the metabolism of *Shewanella* is utilized as a catalyst process to consume fuel and by transferring electrons e⁻ discharged as metabolic waste products of *Shewanella*, electric energy can be extracted. In addition, the ITO electrode generally has high transmittance of visible lights and conductivity and therefore is employed as a transparent electrode.

Considering the context described above, it can be concluded that a dramatic increase in generated current value, found out by the present study, is caused by the increase in the number of *Shewanella* attributable to the current generation, a result of the above item (3), i.e., the phenomenon that the $\alpha\text{-Fe}_2O_3$ fine particles spontaneously agglomerated without an external aid function as the long-distance electron transferring material.

The description was given for $\alpha\text{-Fe}_2O_3$. However, the ferric oxide such as $\alpha\text{-FeOOH}$, $\gamma\text{-Fe}_2O_3$, $\epsilon\text{-Fe}_2O_3$ and $Fe_3O_4$ are also likewise effective as the long-distance electron transferring material.

Ferric sulfide can be also effective as the long-distance electron transferring material as is the case with ferric oxide. In an environment where ferric ions and sulfide ions coexist, when in an ionized state, the ferric sulfide acts as a mediator, whereas when having returned to ferric sulfide, the ferric sulfide acts as the long-distance electron transferring material as is the case with the ferric oxide. Ferric ions and sulfide ions are widely distributed throughout nature. Only ferric ions and sulfide ions generate no ferric sulfide. Bacteria, being microorganisms with a metal-reducing capability (metal-reducing bacteria), can easily produce ferric sulfide from ferric ions and sulfide ions. The produced ferric sulfide functions as a long-distance electron transferring material as is the case with ferric oxide. Besides, it is not easy to synthesize ferric sulfide and it is industrially easier that microorganisms synthesize ferric sulfide by adding ferric ions and sulfide ions than performing a process of adding ferric sulfide to microorganisms.

In manganese oxide, in addition to the effect of the long-distance electron transferring material described above, $Mn^{2+}$ ions partially melted act as a mediator to improve a current generating function.

The present invention is not limited to the present example and various modifications are possible within the scope of the gist of the present invention. In the example described above, the description has been given, e.g., for the case where *Shewanella* was utilized as an example of bacteria, being microorganisms. The present invention is not limited to this case and instead of *Shewanella*, other bacteria, e.g., *Geobacter* that is bacterium (metal-reducing bacterium) with the same metal-reducing cap ability as *Shewanella* or a mixed bio-group, called mix culture, whose type cannot be specified, or bacteria making its habitat in paddy field may be applicable. Microorganisms are effective, such as particularly *Geobacter* (see a document: Molecular Microbiology (2007) 65(1), 12-20) with an extracellular electron transfer capability, *Rhodoferax* group or *Pseudomonas* (see a document: Journal of Japanese society of Microbial Ecology (2008) Vol. 23 No. 2, P. 58).

EXAMPLES

Next, examples of the present invention are described. In addition, it goes without saying that the present invention is not limited to these examples. In addition, *Shewanella loihica* PV-4 and *Shewanella oneidensis* MR-1 which are employed in the examples described below were bought from ATCC (American Type Culture Collection). Among these, a catalogue number (2008 year version) of *Shewanella loihica* PV-4 is BAA-1088 and a catalogue number (2008 year version) of *Shewanella* oneidensis MR-1 is BAA-1096.

Example 1

As metallic oxide, $\alpha$-$Fe_2O_3$ fine particles were employed. A water solution of $\alpha$-$Fe_2O_3$ fine particles is made by dropping an $FeCl_3$ solution into boiling purified water. As microorganism, *Shewanella loihica* PV-4 was employed. For electrochemical measurement, an electrochemical cell 9 shown in FIG. 3 was employed. The electrochemical cell 9 is equipped with an active electrode 10 acting as a negative electrode, a counter electrode 11 acting as a positive electrode, a reference electrode 12 and a reaction tank 13. The active electrode 10, the counter electrode 11 and the reference electrode 12 are electrically connected with a potentiostat acting as an external circuit. Besides, the electrochemical cell 9 is held to a glass plate 14 via a sheet 17 made of silicon rubber

*Shewanella loihica* PV-4 was cultured by the following procedure. A colony stored on an agar culture medium (Marine Broth 20 $gL^{-1}$, Agar 15 $gL^{-1}$) was isolated to be suspended in an MB (Marine Broth 20 $gL^{-1}$) culture medium of 10 ml within a centrifuge tube of 50 ml and then was cultured for one to two nights under an anaerobic condition. An amount of 10 ml of a suspending solution of *Shewanella loihica* PV-4 was centrifugally separated at 3,500 rpm for 10 minutes to allow *Shewanella loihica* PV-4 to be precipitated and thereafter the supernatants were entirely discarded to be converted into an electrolyte of 10 ml as a solution. As an electrolyte, DM-L (10 mM) was employed. Further, after being subjected to shake culture for one night or more, the cultured electrolyte was employed for electrochemical measurement. The shake culture was carried out using BR-40LF (TAITEC) under the condition of 30 degrees C. and 120 rpm.

In addition, DM is the abbreviation of Defined Media and its composition (each indicated in unit of $gL^{-1}$) includes $NaHCO_3$ 2.5, $CaCl_2.2H_2O$ 0.08, $NH_4Cl$ 1.0, $MgCL_2.6H_2O$ 0.2, NaCl 10, 2-[4-(2-Hydroxyethyl)-1-piperaziny]ethane-sulfonic acid (HEPES, a buffering liquid) 7.2. As an electron donor to *Shewanella loihica* PV-4, Sodium Lactate (10 mM) or a yeast extract of 0.5 $gL^{-1}$ for feeding fuel used to allow *Shewanella loihica* PV-4 to generate a minute quantity of required energy were added Hereunder, a DM culture medium containing Lactate is described as, e.g., DM-L (10 mM) and letters in the parenthesis are defined as a Lactate concentration. Further, DM-L was employed, which had been subjected to $N_2$ bubbling for ten minutes or more and to an anaerobic condition.

A 5 ml suspending solution of *Shewanella loihica* PV-4 cultured for electrochemical measurement was centrifugally separated for 10 minutes at 3,500 rpm to precipitate *Shewanella loihica* PV-4. Afterward, all supernatants were discarded to resuspend *Shewanella loihica* PV-4 using a 0.2 ml DM-L (10 mM) and the *Shewanella loihica* PV-4 collected by a syringe was poured into the electrochemical cell 9 through a silicon rubber plug 15 of the electrochemical cell 9. Then, the water solution of the $\alpha$-$Fe_2O_3$ fine particles was poured into the electrochemical cell 9. In addition, inside the electrochemical cell 9, a 4 ml electrolyte acting as a solution was poured in advance. As the electrolyte, the above DM-L (10 mM) was employed.

In the present example, in the electrochemical cell 9, an ITO electrode (the electrode area was 2.0 $cm^2$), a platinum wire, and an Ag|AgCl|$KCl_{sat.}$ electrode were employed as an active electrode 10, a counter electrode 11 and a reference electrode 12, respectively. The Ag|AgCl|$KCl_{sat.}$ electrode is one which was created in such a manner that a silver chloride layer was attached to a surface of a silver member and subsequently the member thus processed was inserted into a water solution of potassium chloride.

For electric measurement, a potentiostat HSV-100 (made by Hokuto Denko) was employed. A potential of the active electrode 10 was fixed at +0.2V over that of the reference electrode 12. Temperature was set at ambient temperature and the electrochemical cell 9 was shielded from light so as not to be exposed to light. The example 1 was practiced by pouring the water solution of the $\alpha$-$Fe_2O_3$ fine particles into the cell 9 so that the concentration of the $\alpha$-$Fe_2O_3$ fine particles inside the cell 9 became 7.5 mM. In the diameter of the $\alpha$-$Fe_2O_3$ fine particle, its first-order particle diameter is on the order of 20 nm and when the particles agglomerate, its diameter gets into hundreds of nm. In this case, the concentration of *Shewanella loihica* PV-4 to DM-L (10 mM) is 2.0 in OD (600 nm) and the concentration of the water solution of the $\alpha$-$Fe_2O_3$ fine particles inside the cell 9 is 7.5 mM as described above. Specifically, the concentration is equivalent to that created by putting $\alpha$-$Fe_2O_3$ fine particles of about 5 mg into a 4 ml solution. In addition, the OD (600 nm) means an intensity of 600 nm light when a microbial suspending solution is put in a cell with 1 cm light path length.

Besides, instead of pouring the water solution of the $\alpha$-$Fe_2O_3$ fine particle in the example 1, a comparative example 1 was practiced by adding iron citrate (III). As for the rest, the same arrangement and conditions as those in the example 1 were applied to the comparative example 1.

Further, instead of pouring the water solution of the $\alpha$-$Fe_2O_3$ fine particles in the example 1, a comparative example 2 was practiced by adding nothing. As for the rest, the same conditions as those in example 1 were applied to the comparative example 2.

Figure 4:
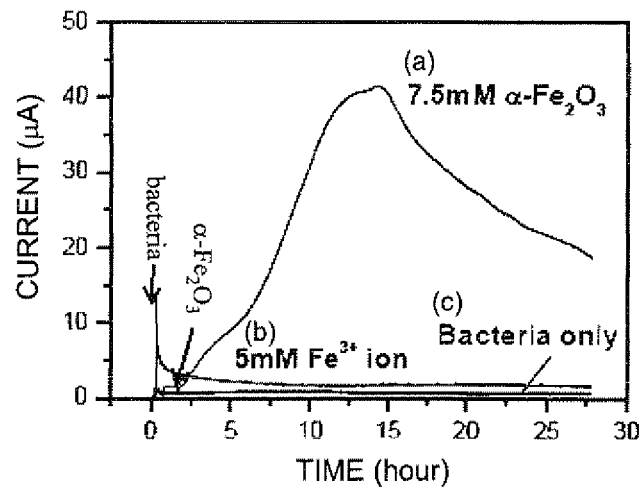
FIG. 4 is a graph illustrating a generated current value measured using the electrochemical cell in the example 1.

The result is shown in FIG. 4. In FIG. 4, (a), (b) and (c) are the results of the example 1, the comparative example 1 and the comparative example 2, respectively. It could be verified that the generated current value obtained in the example 1 was dramatically improved by 50 times or more as compared to that in the case where no $\alpha$-$Fe_2O_3$ fine particle was added.

At the same time, in the comparative example 1 where $Fe^{3+}$ ions were added to DM-L (10 mM) and in the comparative example 2 where nothing was added, such an increase in generated current value as to be obtained when the $\alpha$-$Fe_2O_3$ fine particles were added, was not observed.

Figure 5A:
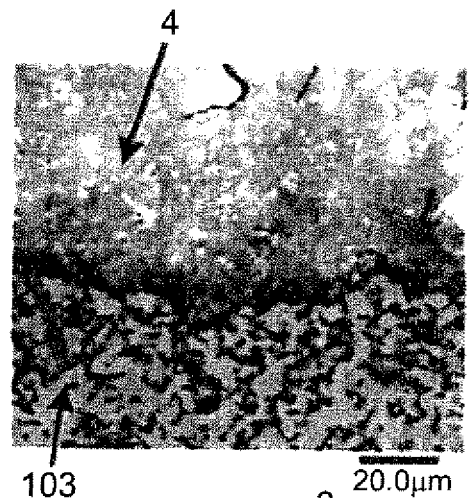
FIG. 5 is an SEM image after 28 hours since a water solution of $\alpha$-$Fe_2O_3$ fine particles was added, (a) a view illustrating a condition in the vicinity of the electrode and (b) an enlarged view of agglomerates
Figure 5B:
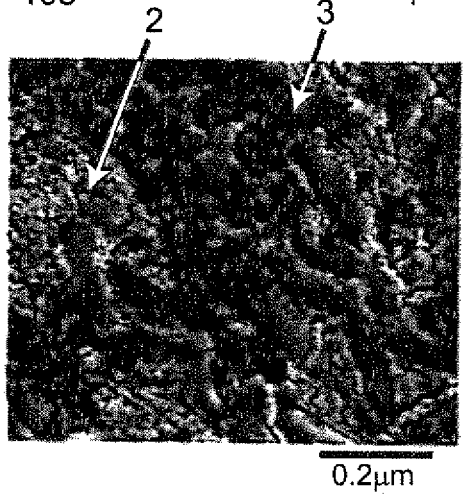

Besides, FIG. 5 shows SEM images after 28 hours have elapsed since the $\alpha$-$Fe_2O_3$ fine particles had been added. It can be learnt that the $\alpha$-$Fe_2O_3$ fine particles acting as the conductive fine particles and the agglomerate 4 of *Shewanella loihica* PV-4 acting as microorganisms have formed a 3-dimensional structure. No $\alpha$-$Fe_2O_3$ fine particle was observed in a position where *Shewanella loihica* PV-4 was absent. Further, when the $\alpha$-$Fe_2O_3$ fine particle was not added, suchlike agglomerate 4 containing *Shewanella* loihica PV-4 was not observed.

These results prove the fact that the $\alpha$-$Fe_2O_3$ fine particles and *Shewanella loihica* PV-4 were coupled strongly to one another and as a result, the 3-dimensionally structured agglomerate 4 was formed. Furthermore, the above results prove the fact that in fact, the $\alpha$-$Fe_2O_3$ fine particles and *Shewanella loihica* PV-4 spontaneously form the agglomerate 4 and the agglomerate 4 functions as the long-distance electron transferring material.

Figure 6:
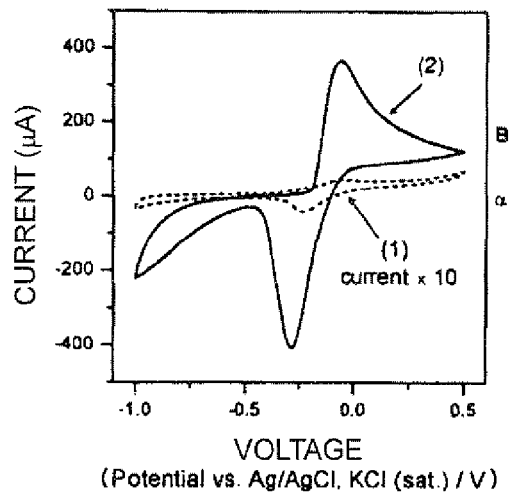
FIG. 6 is a CV curve obtained by measuring using the electrochemical cell.

The dramatic increase in current density, found in the present invention, is due to the fact that the $\alpha$-$Fe_2O_3$a fine particles spontaneously agglomerated and functioned as the long-distance electron transferring material, and whereby *Shewanella loihica* PV-4 attributable to the current generation increased. This can be learnt from the results of the redox potential measurement (CV measurement) performed after current measurement (refer to FIG. 6). Symbols (1), (2) in FIG. 6 are the results of the comparative example 1 and the example 1, respectively. From these results, it could be verified that by adding the $\alpha$-$Fe_2O_3$ fine particles (in the example 1), a larger peak current value could be obtained as compared to the comparative example 1. In addition, the ambient temperature was 30 degrees C. The increase in the redox potential attributable to cytochrome present on the surface of *Shewanella loihica* PV-4 indicates an increase in the number of *Shewanella loihica* PV-4 responsible for current generation. In this manner, an approach of increasing the number of microorganisms responsible for current generation without adding a mediator and increasing the surface area of the electrode to increase a generated current value is a novel invention never before achieved.

Further, in order to verify a function as the long-distance electron transferring material, i.e., a function as a pathway (hereunder, described as a transfer pathway) made available when the $\alpha$-$Fe_2O_3$ fine particles couple together to transfer electrons resulting from a characteristic of an n-type semiconductor over a long distance, an effect of light irradiation on the generated current value was examined. Specifically, if a generated current value at the time of stopping light irradiation is nearly equal to that at the time of performing the light irradiation, the generated current value in this case can be said to be responsible for the thickness of the $\alpha$-$Fe_2O_3$ fine particles. Hence, it was ascertained that by measuring this generated current value, the $\alpha$-$Fe_2O_3$ fine particles functioned as the transfer pathway.

Figure 7A:
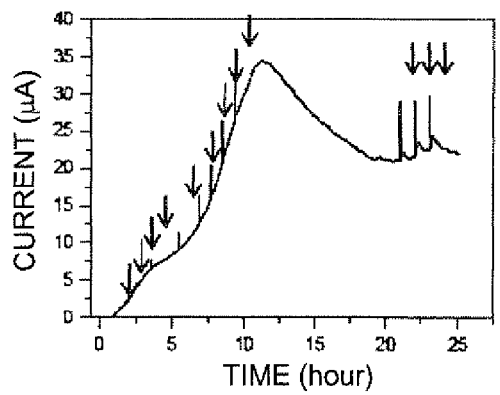
FIG. 7 is a view illustrating an effect of irradiating white light in the example 1, (a) a current change at the time of the irradiation and (b) a magnitude of a photocurrent.
Figure 7B:
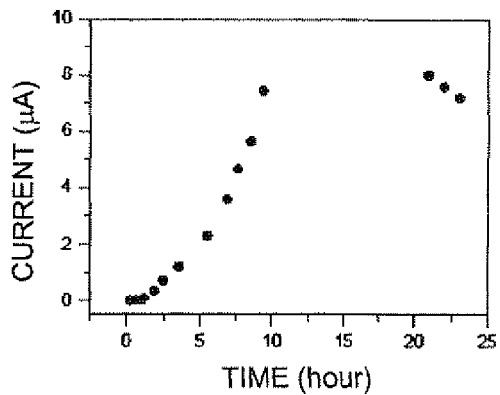

With regard to light irradiation, FIG. 7 shows variations due to white light irradiation (wavelengths of 430 nm or less were cut), in generated current value brought about by *Shewanella loihica* PV-4 when the $\alpha$-$Fe_2O_3$ was added and current (hereunder, referred to as "light current") values generated when light was irradiated. A photoelectric current value was determined by a difference obtained by subtracting a current value just before the light irradiation from a maximum current value during the light irradiation. In addition, the timings of light irradiation were shown by arrows in FIG. 7 (a). Besides, peak currents measured in the case of irradiating light were plotted, as shown in FIG. 7 (b).

With regard to the process in which generated current value increased by *Shewanella loihica* PV-4, it was learnt that the photoelectric current value continued to increase corresponding to a generated current value, and when generated current value reached the maximum value, the generated current value ceased to increase. Here, the $\alpha$-$Fe_2O_3$ possesses a characteristic of an n-type semiconductor and hence an electron in a valence band is photoexcited in the conductive band due to the transition between the bands of $\alpha$-$Fe_2O_3$ to be allowed to move to an electrode, thus causing a photoelectric current. Therefore, if the intensity of light irradiation is constant, the magnitude of a photoelectric current is determined by the thickness of the $\alpha$-$Fe_2O_3$ fine particles which are connected with the ITO electrode and absorb light. This result demonstrates that by making up a 3-dimensional structure, not only the number of the pieces of *Shewanella* loihica PV-4 contributable to the current generation increased, but the $\alpha$-$Fe_2O_3$ fine particles can function as the transfer pathway. In addition, the photoexcitation means a process in which the number of atoms and atomic systems which are within a certain energy level vary depending on absorption of light impinging on a material.

Example 2

Unlike the example 1, a graphite electrode was employed as the active electrode 10 of the electrochemical cell 9, whereas the rest part of its arrangement and conditions remained the same as those of the example 1 (example 2). Further, BR-40LF (TAITEC) was employed to perform shake culture of *Shewanella loihica* PV-4 under the condition of 30 degrees C. and 120 rpm. In addition, the graphite electrode is made of a powder sintered body containing carbon as its main component. According to the present example, a graphite electrode was employed, instead of an ITO electrode, since light irradiation was not carried out.

Further, unlike the example 2, in a comparative example 3, nothing was added to the microorganisms instead of pouring a water solution of $\alpha$-$Fe_2O_3$ fine particles to the electrochemical cell 9, whereas the rest remained the same as those of the example 2.

Figure 8:
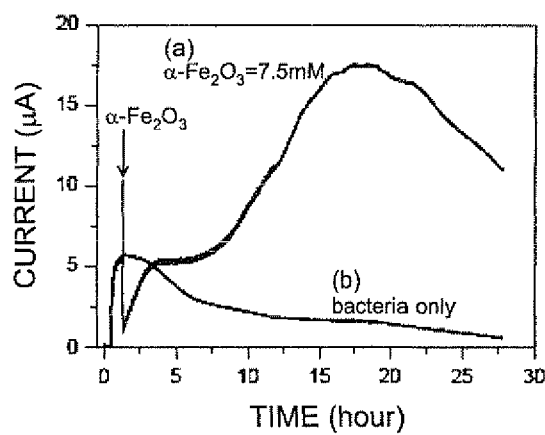
FIG. 8 is a graph illustrating a generated current value measured using the electrochemical cell in the example 2.

The result of the example 2 is shown in FIG. 8. FIG. 8 (a) represents the result of the example 2, while FIG. 8 (b) represents the result of the comparative example 3. As is clearly shown in FIG. 8, such an increase in generated current value as that in the example 1 was also observed in the example 2. In the comparative example 3 where nothing was added, there could not be observed such an increase in generated current value as to be achieved in the case where $\alpha$-$Fe_2O_3$ fine particles. According to the result and microbial fuel cell 1 of the present invention, the same effect as that in the example 1 in which an ITO electrode was employed could be achieved even if a graphite electrode was employed as the active electrode 10.

Example 3

Unlike the example 1, in an example 3, *Shewanella oneidensis* MR-1 was employed as microorganisms, whereas the rest part of its arrangement and conditions remained the same as those of the example 1 (example 3). Further, BR-40LF (TAITEC) was employed to perform shake culture of *Shewanella* oneidensis MR-1 under the condition of 30 degrees C. and 120 rpm.

Further, unlike the example 3, in a comparative example 4, nothing was added to the microorganisms instead of pouring a water solution of $\alpha$-$Fe_2O_3$ fine particles to the electrochemical cell 9, whereas the rest remained the same as those of the example 3.

Figure 9:
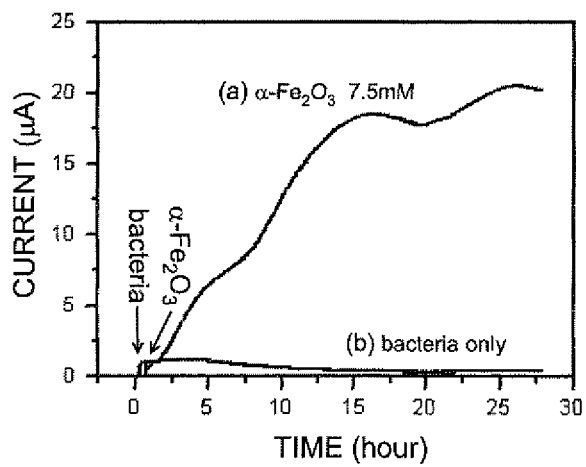
FIG. 9 is a graph illustrating a generated current value measured using the electrochemical cell in the example 3.

The result of the example 3 is shown in FIG. 9. FIG. 9(*a*) represents the result of the example 3, while FIG. 9 (*b*) represents the result of the comparative example 4. As is clear from FIG. 9, such a significant increase in generated current value as that obtained in the example 1 was also observed in the example 3. In the comparative example 4 where nothing was added, such an increase in generated current value as to be achieved in the case where $\alpha$-$Fe_2O_3$ fine particles were added was not observed. According to such a result, in the microbial fuel cell 1 of the present invention, it was verified that the same effect as that obtained in the example 1 in which *Shewanella loihica* PV-4 was employed could be achieved even if *Shewanella loihica* MR-1 was employed as microorganisms.

Example 4

An example 4 in which ferric sulfide fine particles were employed as the conductive fine particles is described hereinafter. *Shewanella loihica* PV-4 was cultured in the similar way as was done in the example 1 in an environment in which $Fe^{3+}$ ions and $S_2O_3^{2-}$ ions coexist. A colony stored on an agar medium (Marine Broth 20 $gL^{-1}$, Agar 15 $gL^{-1}$) was cultured under an anaerobic condition for one night. Further, BR-40LF (TAITEC) was employed to perform shake culture of *Shewanella loihica* PV-4 under the condition of 30 degrees C. and 120 rpm. At that time, $Fe^{3+}$ was reduced to $Fe^{2+}$, and $S_2O_3^{2-}$ was reduced to $S^{2-}$, thereby producing FeS. The first-order particle diameter of a ferric sulfide fine particle is approximately 20 nm, but becomes hundreds of nm when the particles agglomerate. After subjected to centrifugal separation, the suspending solution of *Shewanella loihica* PV-4 was poured through a silicon rubber plug 15 of the electrochemical cell 9 for electrochemical measurement. In this case, the concentration of *Shewanella loihica* PV-4 to DM-L (10 mM) was 2.0 in OD (600 nm), and the concentration of a water solution of ferric sulfide fine particles inside the electrochemical cell 9 was 7.5 mM.

Figure 10:
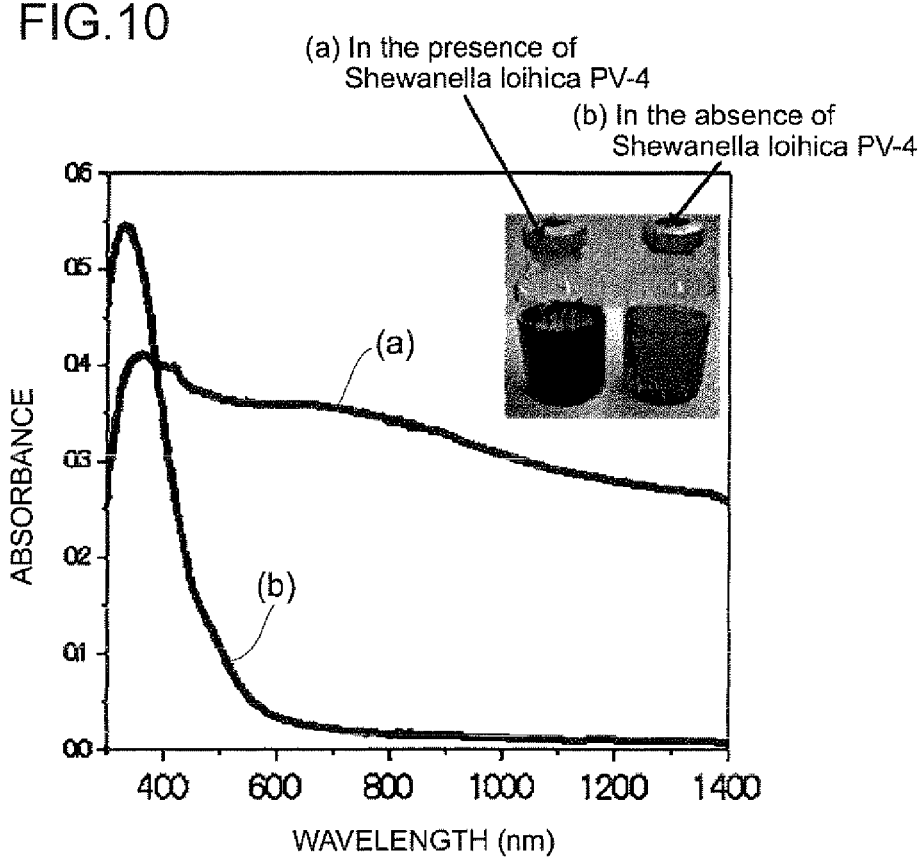
FIG. 10 is a view illustrating a photograph of precipitates and an absorption spectrum of the precipitates in the example 4.

A picture and an absorption spectrum of the precipitate thus obtained (20 days after culturing) are shown in FIG. 10. In FIG. 10, (a) represents the precipitate in the presence of *Shewanella loihica* PV-4, while (b) represents the precipitate in the absence of *Shewanella loihica* PV-4. The formation of black precipitates was observed in the presence of *Shewanella loihica* PV-4. Further, since the absorption spectrum of the black precipitates reached near infrared region, the black precipitates were proved to be ferric sulfide. However, the observed absorption spectrum up to 600 nm in the absence of *Shewanella loihica* PV-4 was caused by ferric hydroxide.

Figure 11:
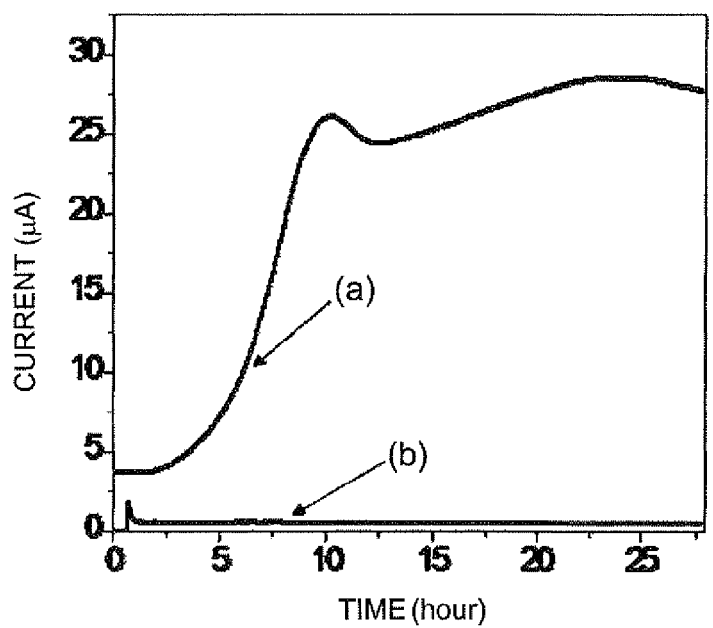
FIG. 11 is a graph illustrating a generated current value measured using the electrochemical cell in the example 4.

FIG. 11 is a current versus time chart when the ferric sulfide fine particles thus obtained and the suspending solution of *Shewanella loihica* PV-4 were poured into the electrochemical cell 9. In FIG. 11, (a) represents the result of a case in which ferric sulfide fine particles were present (Example 4), whereas (b) represents the result of a case in which ferric sulfide fine particles were absent (only *Shewanella loihica* PV-4 existed in a comparative example 5). According to the present example, the generated current value dramatically increased by 30 times as compared to that obtained in the case where ferric sulfide fine particles were absent. This result indicates that the same effect as that in the example 1 in which $\alpha$-$Fe_2O_3$ was employed could also be achieved for the ferric sulfide fine particles.

Example 5

Figure 12:
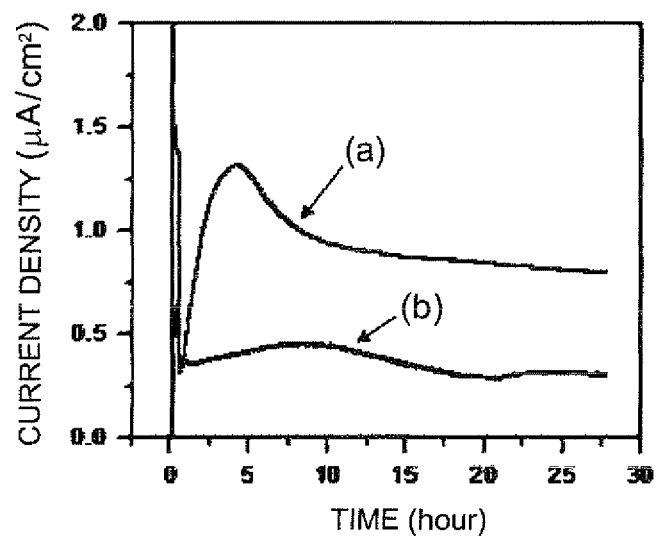
FIG. 12 is a graph illustrating a current density measured using the electrochemical cell in the example 5.

Unlike the example 1, an example 5 is described hereinafter, in which $\gamma$-$Fe_2O_3$ fine particles were employed as the conductive fine particles (the example 5). Except using $\gamma$-$Fe_2O_3$ fine particles as the conducive fine particles, the example 5 employed the same method as that of the example 1 to culture *Shewanella loihica* PV-4 under an anaerobic condition. Further, BR-40LF (TAITEC) was employed to perform shake culture of *Shewanella loihica* PV-4 under the condition of 30 degrees C. and 120 rpm. The first-order particle diameter of a $\gamma$-$Fe_2O_3$ fine particle is approximately 20 nm, but becomes hundreds of nm when the particles agglomerate. FIG. 12 shows a current density versus time chart when a water solution of the $\gamma$-$Fe_2O_3$ fine particles obtained by dissolving the $\gamma$-$Fe_2O_3$ fine particles in purified water was poured into the electrochemical cell 9 so that the concentration inside the cell became 7.5 mM. In addition, in this case, the concentration of *Shewanella loihica* PV-4 to DM-L (10 mM) was 2.0 in OD (600 nm), and the concentration of the water solution of the $\gamma$-$Fe_2O_3$ fine particles inside the cell was 7.5 mM as mentioned above. Specifically, the concentration was equivalent to that created by putting the $\gamma$-$Fe_2O_3$ fine particles of about 5 mg into a 4 ml solution. In FIG. 12, (a) represents the result of a case in which the $\gamma$-$Fe_2O_3$ fine particles were present (the example 5), whereas (b) represents the result of a case in which the $\gamma$-$Fe_2O_3$ fine particles were absent (only *Shewanella loihica* PV-4 existed, in a comparative example 6). According to the present example, the current density substantially doubled as compared to that obtained in the case in which the $\gamma$-$Fe_2O_3$ fine particles were absent.

In addition, the $\gamma$-$Fe_2O_3$ fine particles were produced according to a method described in a document (Y. S. Kang, S. Risbud, J. F. Rabolt, P. Stroeve Chem. Mater., 1996, 8, 2209). In the beginning, $FeCl_3 \times 6H_2O$ (52 mM) and $FeCl_2 \times 4H_2O$ (26 mM) were dissolved in 40 ml of nitrogen saturated ultrapure water, in a manner that the molar ratio between $FeCl_3 \times 6H_2O$ and $FeCl_2 \times 4H_2O$ became 2:1, followed by adding 1.4 ml of concentrated hydrochloric acid to the solution thus obtained. Next, the solution thus obtained was dropped into 415 ml of a NaOH solution with 1.5M while carrying out intensive stirring. Black precipitates were produced due to the dropping of the aforementioned solution, and the supernatants thereof were discarded, followed by cleansing the precipitates with an ultrapure water for several times, and adding concentrated hydrochloric acid to neutralize the solution as a whole, thereby obtaining a solution of $Fe_3O_4$. From the solution of $Fe_3O_4$ synthesized in the above manner, $Fe_3O_4$ was precipitated and dried to be collected as a powder. Further, after heating the powders at a temperature of 250 degrees C. for three hours, the $\gamma$-$Fe_2O_3$ fine particles were obtained.

Example 6

Figure 13:
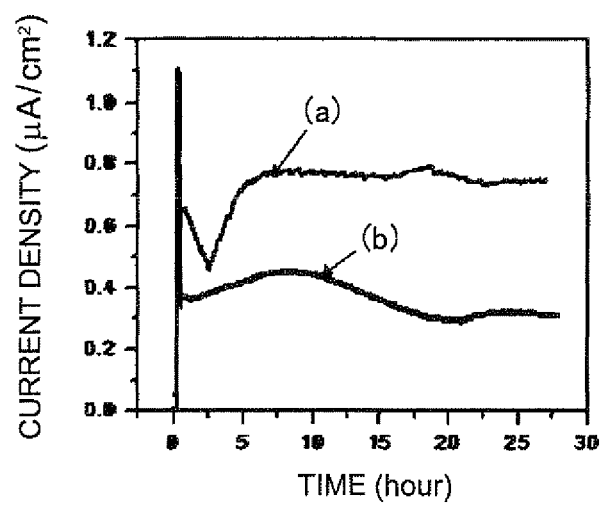
FIG. 13 is a graph illustrating a current density measured using the electrochemical cell in the example 6.

An example 6 is described hereinafter in which $\epsilon$-$Fe_2O_3$ fine particles were employed as the conductive fine particles (the example 6), differently from the example 1. Except using the $\epsilon$-$Fe_2O_3$ fine particles as the conducive fine particles, the example 6 employed the same method as that in the example 1 to culture *Shewanella loihica* PV-4 under an anaerobic condition. Further, BR-40LF (TAITEC) was employed to perform shake culture of *Shewanella loihica* PV-4 under the condition of 30 degrees C. and 120 rpm. The first-order particle diameter of a $\epsilon$-Fe$_2$O$_3$ fine particle is approximately 20 nm, but becomes hundreds of nm when the particles agglomerate. FIG. 13 shows a current density versus time chart when a water solution of the $\epsilon$-Fe$_2$O$_3$ fine particles obtained by dissolving the $\epsilon$-Fe$_2$O$_3$ fine particles in purified water was poured into the electrochemical cell 9 so that the concentration inside the cell became 7.5 mM. In addition, in this case, the concentration of *Shewanella loihica* PV-4 to DM-L (10 mM) was 2.0 in OD (600 nm), and the concentration of the water solution of the $\epsilon$-Fe$_2$O$_3$ fine particles inside the electrochemical cell 9 was 7.5 mM as mentioned above. Specifically, the concentration was equivalent to that created by putting the $\epsilon$-Fe$_2$O$_3$ fine particles of about 5 mg into a 4 ml solution. In FIG. 13, (a) represents the result of a case in which $\epsilon$-Fe$_2$O$_3$ fine particles were present as the conductive fine particles (the example 6), whereas (b) represents the result of a case in which the $\epsilon$-Fe$_2$O$_3$ fine particles were absent (only *Shewanella loihica* PV-4 existed in a comparative example 7). According to the present example, the current density substantially doubled as compared to that obtained in the case in which the $\epsilon$-Fe$_2$O$_3$ fine particles were absent.

In addition, the $\epsilon$-Fe$_2$O$_3$ fine particles were produced according to a method described in a document (Journal of the Physical Society of Japan, Vol. 74, No. 7, July, 2005, pp. 1946-1949). More specifically, in the beginning, a micellar solution was obtained by dissolving a surface-active agent (such as cetyltrimethylammonium bromide) on the aqueous phase of a solution having n-octane as its oil phase. Ferric nitrate (III) and indium nitrate (III) are dissolved in this micellar solution and barium nitrate is added thereto as a shape-control agent, thereby obtaining a raw material solution. Also, in addition to obtaining such raw material solution, a neutralizer solution was obtained by mixing the neutralizer such as a water solution of ammonia with a micellar solution obtained by dissolving a surface-active agent (such as cetyltrimethylammonium bromide) on the aqueous phase of a solution having n-octane as its oil phase.

Subsequently, using a reverse-micelle method, a mixed solution was produced by stirring and mixing both the aforementioned raw material solution and the neutralizer solution. An appropriate amount of tetraethylorthosilane solution was added to this mixed solution as a silane compound, thereby covering the surfaces of ferric hydroxide compound particles with silica via a sol-gel method so as to produce silica-covered ferric hydroxide compound particles.

Next, the silica-covered ferric hydroxide compound particles were separated from the mixed solution, and subjected to a baking treatment at a predetermined temperature (within 700 to 1300 degrees C.) under the atmospheric condition. Through such baking treatment, microscopic $\epsilon$-Fe$_2$O$_3$ fine particles were produced due to the oxidation reaction inside the silica shell in the silica-covered ferric hydroxide compound particles.

Example 7

Figure 14:
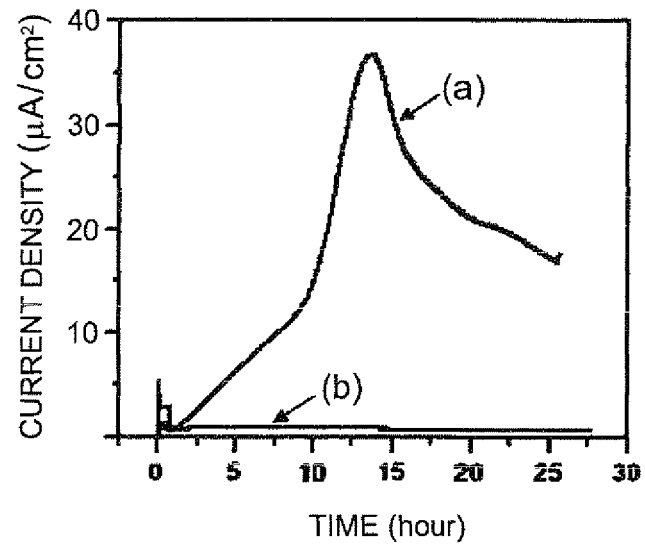
FIG. 14 is a graph illustrating a current density measured using the electrochemical cell in the example 7.

Unlike the example 1, an example 7 is described hereinafter, in which $\alpha$-FeOOH fine particles were employed as the conductive fine particles. Except using $\alpha$-FeOOH fine particles as the conducive fine particles, the example 7 employed the same method as that of the example 1 to culture *Shewanella loihica* PV-4 under an anaerobic condition. Further, BR-40LF (TAITEC) was employed to perform shake culture of *Shewanella loihica* PV-4 under the condition of 30 degrees C. and 120 rpm. The first-order particle diameter of the $\alpha$-FeOOH fine particle is approximately 20 nm, but becomes as long as hundreds of nm when the particles agglomerate. FIG. 14 shows a current density versus time chart when a water solution of the $\alpha$-FeOOH fine particles was poured into the electrochemical cell 9 so that the concentration inside the cell became 7.5 mM. In addition, in this case, the concentration of *Shewanella loihica* PV-4 to DM-L (10 mM) was 2.0 in OD (600 nm), and the concentration of the water solution of the $\alpha$-FeOOH fine particles inside the electrochemical cell 9 was 7.5 mM as mentioned above. In FIG. 14, (a) represents the result of a case in which $\alpha$-FeOOH fine particles were employed (an example 8), whereas (b) represents the result of a case in which $\alpha$-FeOOH fine particles were absent (only *Shewanella loihica* PV-4, as in a comparative example 8). According to the present example, the current density dramatically increased (by approximately 50 times) as compared to that obtained in the case in which the $\alpha$-FeOOH fine particles were absent (only *Shewanella loihica* PV-4, an in a comparative example 8). However, a decrease in the current density observed after 15 hours was caused by the consumption of lactate employed as a fuel.

In addition, the water solution of the $\alpha$-FeOOH fine particles was produced according to a method described in a document (Ref. R. J. Atkinson, A. M. Posner, and J. P. Quirk J. Phys. Chem., 1967, 71, 550). In the beginning, 40 ml of a NaOH solution with 2.5M was added to 160 ml of a FeCl$_3$ solution with 0.1M, followed by heating the solution thus obtained at a temperature of 60 degrees C. for 24 hours. Subsequently, the solution thus obtained was dialyzed with a dialysis membrane (molar weight cut into 6000 to 8000) made of cellulose, thereby obtaining the water solution of the $\alpha$-FeOOH fine particles.

Example 8

Figure 15:
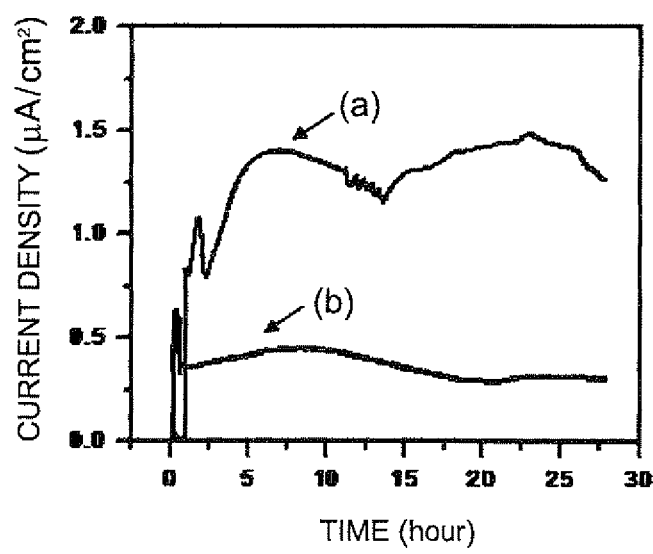
FIG. 15 is a graph illustrating a current density measured using the electrochemical cell in the example 8.

Unlike the example 1, an example 8 is described hereinafter, in which Fe$_3$O$_4$ fine particles were employed as the conductive fine particles. Except using the Fe$_3$O$_4$ fine particles as the conducive fine particles, the example 8 employed the same method as that of the example 1 to culture *Shewanella loihica* PV-4 under an anaerobic condition. Further, BR-40LF (TAITEC) was employed to perform shake culture of *Shewanella loihica* PV-4 under the condition of 30 degrees C. and 120 rpm. The first-order particle diameter of a Fe$_3$O$_4$ fine particle is approximately 20 nm, but becomes hundreds of nm when the particles agglomerate. FIG. 15 shows a current density versus time chart when a water solution of the Fe$_3$O$_4$ fine particles was poured into the electrochemical cell 9 so that the concentration inside the cell became 7.5 mM. In addition, in this case, the concentration of *Shewanella loihica* PV-4 to DM-L (10 mM) was 2.0 in OD (600 nm), and the concentration of the water solution of the Fe$_3$O$_4$ fine particles inside the electrochemical cell 9 was 7.5 mM as mentioned above. Specifically, the concentration is equivalent to that created by putting the Fe$_3$O$_4$ fine particles of about 5 mg into a 4 ml solution. In FIG. 15, (a) represents the result of a case in which the Fe$_3$O$_4$ fine particles were present (in the example 8), whereas (b) represents the result of a case in which the Fe$_3$O$_4$ fine particles were absent (only *Shewanella loihica* PV-4 in a comparative example 9). According to the present example, the current density substantially tripled as compared to that obtained in the case in which the Fe$_3$O$_4$ fine particles were absent (only *Shewanella loihica* PV-4, in the comparative example 9).

In addition, the water solution of the $Fe_3O_4$ fine particles was produced according to a method described in a document (Ref. Y. S. Kang, S. Risbud, J. F. Rabolt, P. Stroeve Chem. Mater., 1996, 8, 2209). In the beginning, $FeCl_3 \times 6H_2O$ (52 mM) and $FeCl_2 \times 4H_2O$ (26 mM) were dissolved in 40 ml of a nitrogen saturated ultrapure water so that the molar ratio between $FeCl_3 \times 6H_2O$ and $FeCl_2 \times 4H_2O$ became 2:1, followed by adding 1.4 ml of concentrated hydrochloric acid to the solution thus obtained. Next, the solution thus obtained was dropped into 415 ml of a NaOH solution with 1.5M while carrying out intensive stirring. Black precipitates were produced due to the dropping of the aforementioned solution, and the supernatants thereof were discarded, followed by cleansing the precipitates with an ultrapure water for several times, and further adding concentrated hydrochloric acid to neutralize the solution, thereby obtaining the water solution of the $Fe_3O_4$ fine particles.

Example 9

Figure 16:
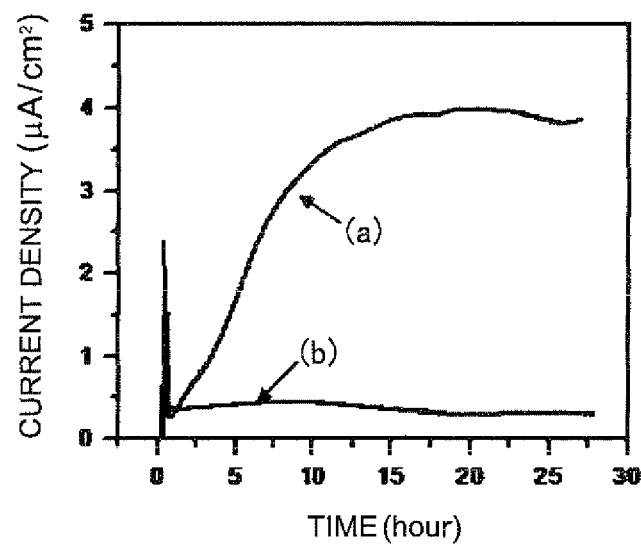
FIG. 16 is a graph illustrating a current density measured using the electrochemical cell in the example 9.

Unlike the example 1, an example 9 is described hereinafter, in which manganese oxide ($MnO_2$) fine particles were employed as the conductive fine particles. Except using the manganese oxide fine particles as the conducive fine particles, the example 9 employed the same method as that of the example 1 to culture *Shewanella loihica* PV-4 under an anaerobic condition. Further, BR-40LF (TAITEC) was employed to perform shake culture of *Shewanella loihica* PV-4 under the condition of 30 degrees C. and 120 rpm. The first-order particle diameter of the manganese oxide fine particle is approximately 20 nm, but becomes hundreds of nm when the particles agglomerate. FIG. 16 shows a current density versus time chart when a water solution of the manganese oxide fine particles obtained by dissolving manganese oxide fine particles in purified water was poured into the electrochemical cell 9 so that the concentration inside the cell became 7.5 mM. In addition, in this case, the concentration of *Shewanella loihica* PV-4 to DM-L (10 mM) was 2.0 in OD (600 nm), and the concentration of the water solution of the manganese oxide fine particles inside the electrochemical cell 9 was 7.5 mM as mentioned above. In FIG. 16, (a) represents the result of a case in which the manganese oxide fine particles were present (the example 9), whereas (b) represents the result of a case in which the manganese oxide fine particles were absent (only *Shewanella loihica* PV-4, in a comparative example 10). According to the present example, the current density octupled as compared to that obtained in the case in which the manganese oxide fine particles were absent (only *Shewanella loihica* PV-4, in the comparative example 10).

In addition, the manganese oxide fine particles were produced according to a method described in document (Ref. R. M. McKenzie Mineral. Mag., 1971, 38, 493). In the beginning, a $Mn(NO_3)_3$ solution was heated so that its moisture was almost evaporated, and was further heated at a temperature of 180 degrees C. for 48 hours. The solid substance thus obtained was then dissolved in a concentrated hydrochloric acid, and the solution thus obtained was further dropped into ultrapure water while being subjected to filtration. Dark brown precipitates were obtained, followed by cleansing as well as filtering the same to obtain the manganese oxide fine particles.

Example 10

An example 10 is described hereinafter, in which microorganisms collected from a paddy soil were employed. The example 10 examined the case in which $\alpha$-$Fe_2O_3$ fine particles were employed as the conductive fine particles and the case in which the $Fe_3O_4$ fine particles were employed as the conductive fine particles. In addition, $\alpha$-$Fe_2O_3$ fine particles were produced using the same procedures as described in the example 1, while $Fe_3O_4$ fine particles were produced using the same procedures as described in the example 8.

The microorganisms collected from a paddy soil were cultured using the following procedures. First of all, 12 mL of a PS culture medium was employed to culture the microorganisms. When culturing the microorganisms, sodium acetate (10 mM) was added as an electron donor. As a source of microorganisms, 20 mg (wet weight) of the paddy soil was added to the PS culture medium. The microorganisms were cultured at a temperature of 30 degrees C., and sodium acetate (10 mM) was added again when the current density was in low level (due to deficiency in acetic acid).

In addition, the PS culture medium comprises $NH_4Cl$ 10 mM, $KH_2PO_4$ 1 mM, $MgCl_2$ 0.5 mM, $CaCl_2$ 0.5 mM. $NaHCO_3$ 5 mM, HEPES 10 mM, and Yeast extract 0.5 g/L.

Sodium Acetate (10 mM) was added as an electron donor to the microorganisms, and 0.5 $gL^{-1}$ of yeast extract was also added to supply fuel required for the microorganisms in minute amounts.

Figure 3A:
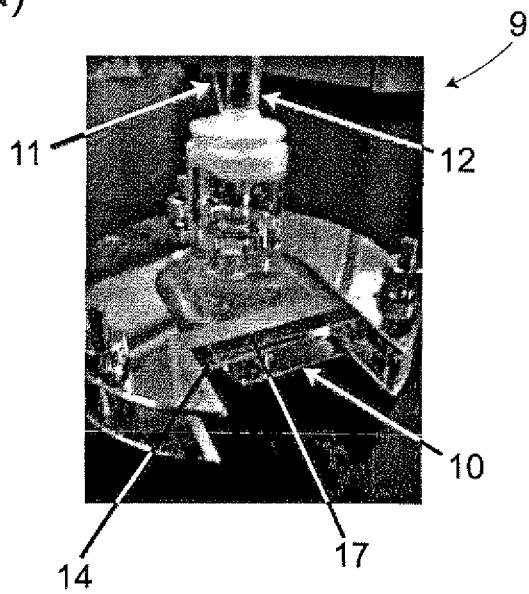
FIG. 3 is a view illustrating a structure of an electrochemical cell according to examples, (a) its perspective view and (b) its cross-sectional view.
Figure 3B:
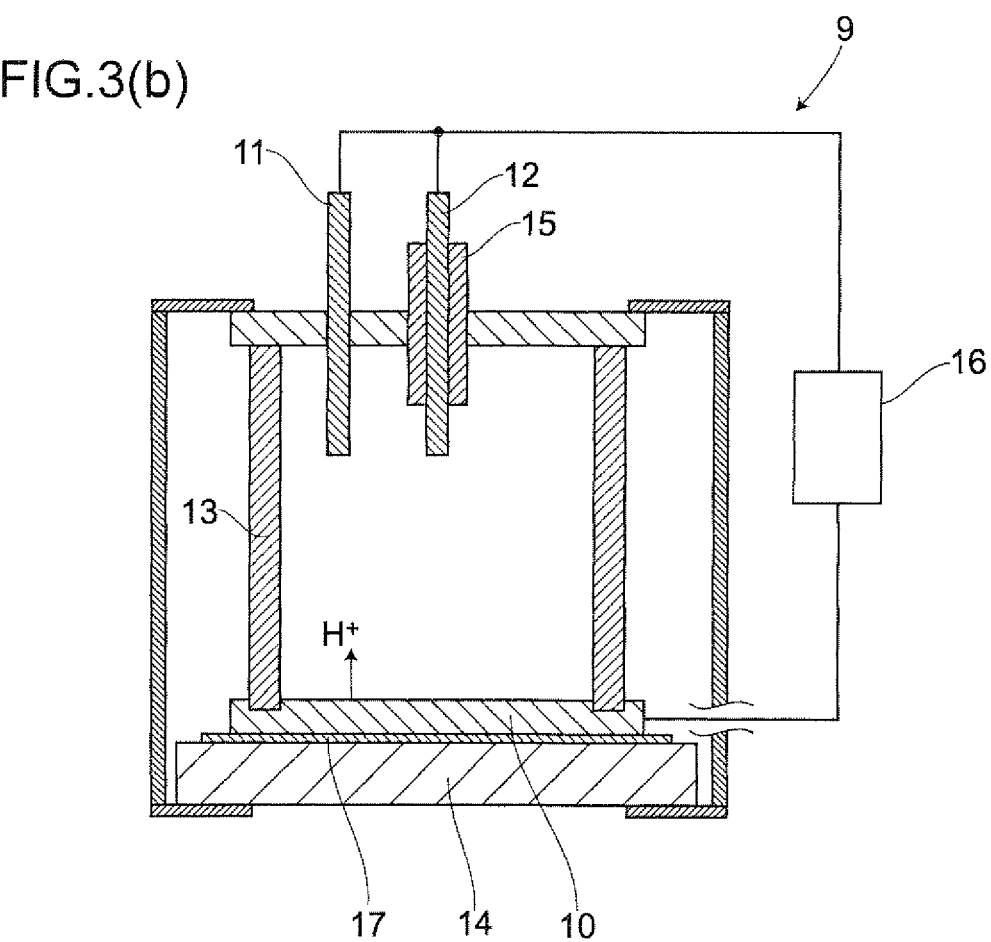

For electrochemical measurement, an electrochemical cell 9 shown in FIG. 3 was employed. An ITO electrode (2.8 cm in diameter, 6.2 $cm^2$ in electrode area), a platinous wire, and an Ag|AgCl|KCl$_{sat}$. electrode were employed as an active electrode 10, a counter electrode 11 and a reference electrode 12, respectively. The electrochemical cell 9 was held by a glass plate 14. Further, 4.0 ml of an electrolyte acting as a solution was poured into the electrochemical cell 9 in advance. The DM-L (10 mM) was employed as the electrolyte.

Such electrolyte was subjected to $N_2$ bubbling for ten minutes or more to create an anaerobic condition, and then used for electrochemical measurement. A 5 ml suspending solution of the microorganisms cultured for electrochemical measurement was centrifugally separated for 10 minutes at 3,500 rpm, to precipitate the microorganisms. Afterward, all supernatants were discarded to resuspend the microorganisms with 0.2 ml DM-L (10 mM). The suspending solution thus obtained was collected by a syringe, and was poured into the electrochemical cell 9 through the silicon rubber plug 15.

HSV-100 (made by Hokuto Denko) was employed for electrical measurement. The electric potential of the active electrode 10 was set as +0.2V to the reference electrode 12. The measurement was carried out at an ambient temperature, and light shielding was laid to prevent the electrochemical cell 9 from being exposed to light. In an example 10 (1), the water solution of the $\alpha$-$Fe_2O_3$ fine particles, described above, was poured to render the fine-particulate concentration into 5 mM. In an example 10 (2), the water solution of $Fe_3O_4$ fine particles was poured to render the fine-particulate concentration into 3.3 mM. The first-order particle diameter of a $\alpha$-$Fe_2O_3$ fine particle is approximately 20 nm, but becomes hundreds of nm when the particles agglomerate. In this case, the concentration of the paddy-soil microorganisms to DM-L (10 mM) was 2.0 in OD (600 nm), while the $\alpha$-$Fe_2O_3$ fine particles and the $Fe_3O_4$ fine particles were added so that the concentration made up of both the particles became 10 mM in terms of Fe atoms.

Unlike the example 10, instead of adding the water solution of the $\alpha$-$Fe_2O_3$ fine particles and the water solution of $Fe_3O_4$ fine particles, in a comparative example 11, nothing was added to the microorganisms. However, the rest part of the comparative example 11 remains the same as the example 10.

Figure 17:
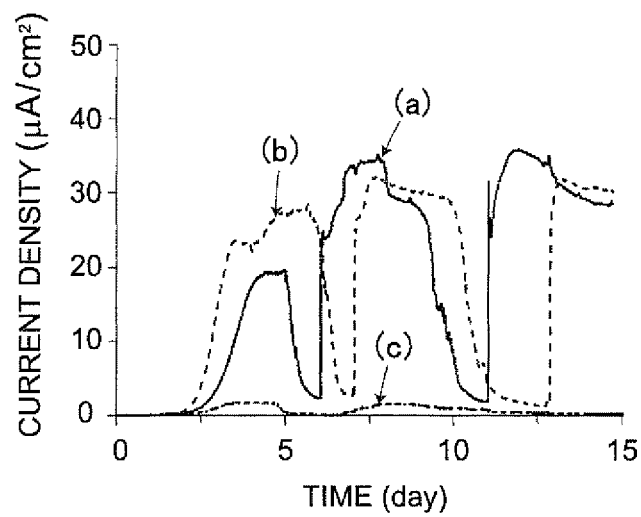
FIG. 17 is a graph illustrating a current density measured using the electrochemical cell in the example 10.

The results of the example 10 and the comparative example 11 are shown in FIG. 17. In FIG. 17, (a) represents the result when the α-$Fe_2O_3$ fine particles were added (the example 10 (1)), whereas (b) represents the result when the $Fe_3O_4$ fine particles were added (the example 10 (2)), and (c) represents the result of the comparative example 11. When the microorganisms collected from the paddy soil were employed, the current density observed in the example 10 was dramatically improved by 50 times or more as compared to that of the comparative example 11 in which neither α-$Fe_2O_3$ fine particles nor $Fe_3O_4$ fine particles were added.

However, in the comparative example 11 in which no conducive fine particle was added, such a significant increase in current density as to be obtained in the case in which α-$Fe_2O_3$ fine particles were added was not observed.

A group of genes of the microorganisms inside a biofilm formed on the surface of the electrodes after culturing, was analyzed using the 16S rRNA gene clone library method.

In the beginning, DNA was extracted from the microorganisms inside the biofilm formed on the surface of the electrodes, using a FastDNA Spin Kit for Soil (MP bio). Next, the DNA was amplified by applying a unique primer (27F:5'-AGAGTTTGATCCTGGCTCAG, 517R: ATACCGCGGCT-GCTGG) to a bacterial 16S rRNA gene, using a polymerase chain reaction method (PCR). The PCR products thus obtained were cloned in a pGEM-T Easy vector (Promega), and then, introduced to *E. coli* JM109 (Promega) to clone the products.

Further, the analysis of the sequence (using a sequencer made by Takara Co., Ltd.) cloned was carried out. The result of the sequence analysis shows that 21/48 clones (44%) in the example 10 (1) in which the α-$Fe_2O_3$ fine particles were added, and 17/48 clones (35%) in the example 10 (2) in which $Fe_3O_4$ was added, were each found to possess a sequence approximate to *Geobacter* group. In addition, in the comparative example 11 in which conductive fine particles were not added, 7/48 clones (15%) were found to possess a sequence approximate to *Geobacter* group. Further, the rate of the *Geobacter* group in the original paddy soil was found to be 1% or less.

Industrial Application Potency Of The Present Invention

Nowadays, there has been known many studies on chemical fuel cells using platinum. However, the platinum itself is highly rare and expensive. Further, such a chemical fuel cell hardly contributes to a carbon dioxide reduction, due to the difficulty of removing carbon when hydrogen is produced. A microbial fuel cell capable of directly generating electrons from microorganisms is simple in structure and is characterized by carbon neutral (while carbon dioxide is generated, the flow of carbon cycling is not deranged due to the independence of fossil fuel). In this sense, the microbial fuel cell of the present invention, which can significantly increase the current density thereof, should be highly useful.

Explanation Of The Reference Numbers 1. microbial fuel cell
2. conductive fine particle
3. microorganism
4. agglomerate
9. electrochemical cell
10. active electrode (negative electrode)
11. counter electrode
12. reference electrode
13. reaction tank
14. glass plate
15. silicon rubber tap
16. potentiostat (outer circuit)
17. silicon rubber sheet
100. microbial fuel cell
103. electrode
301, 302 microorganism

The invention claimed is:

1. A microbial fuel cell equipped with a pair of electrodes and an external circuit electrically connecting a pair of said electrodes, wherein on a negative electrode that is one of said electrodes, 3-dimensionally structured agglomerates are spontaneously formed in a solution containing conductive fine particles and microorganisms with an extracellular electron transfer capability, said 3-dimensionally structured agglomerates being formed from said conductive fine particles and microorganisms by allowing said microorganisms to specifically adsorb said conductive fine particles; and said microorganisms are held by said conductive fine particles over a range of zone extending vertically away from a surface of said negative electrode, in a manner such that said conductive fine particles are distributed among said microorganisms; and said conductive fine particles comprise α-$Fe_2O_3$, α-FeOOH, γ-$Fe_2O_3$, ε-$Fe_2O_3$ or $Fe_3O_4$ or ferric sulfide, and then said conductive fine particles transfer electrons from said microorganisms to said negative electrode.

2. The microbial fuel cell according to claim 1, wherein said conductive fine particles include ferric oxide.

3. The microbial fuel cell according to claim 1, wherein said conductive fine particles are obtained by biosynthesis of microorganisms in an environment where ferric ions and sulfide ions coexist, said microorganisms being metal-reducing bacteria.

4. The microbial fuel cell according to claim 1, wherein said conductive fine particles include manganese oxide.

5. The microbial fuel cell according to claim 3, wherein said metal-reducing bacteria include bacteria of a *Shewanella* group, a *Geobacter* group, a *Rhodoferax* group or a *Pseudomonas* group.

6. The microbial fuel cell according to claim 3, wherein said metal-reducing bacteria contain *Shewanella loihica* or *Shewanella oneidensis*.

7. The microbial fuel cell according to claim 1, wherein said 3-dimensionally structured agglomerates are spontaneously formed by mixing said conductive fine particles and said microorganisms in said solution.

8. The microbial fuel cell according to claim 7, wherein said 3-dimensionally structured agglomerates comprises agglomerates of conductive fine particles.

9. The microbial fuel cell according to claim 1, wherein said 3-dimensionally structured agglomerates comprises agglomerates of conductive fine particles.

10. A method for manufacturing a negative electrode of a pair of electrodes used in a microbial fuel cell that is equipped with said pair of electrodes and an external circuit electrically connected thereto, comprising:
a step of preparing a solution for said negative electrode by mixing conductive fine particles and microorganisms with an extracellular electron transfer capability;
a step of allowing said conductive fine particles to hold said microorganisms over a range of zone extending vertically away from a surface of said negative electrode, in a manner such that said conductive fine particles disperse among said microorganisms and are further coupled to one another to hold said microorganisms; and;
a step of causing 3-dimensionally structured agglomerates to be spontaneously formed by allowing said microorganisms to specifically adsorb said conductive fine particles.

11. The method for manufacturing the negative electrode according to claim 10, wherein said microorganisms are metal-reducing bacteria.

12. The method for manufacturing the negative electrode according to claim 11, wherein said metal-reducing bacteria include bacteria of a *Shewanella* group, a *Geobacter* group, a *Rhodoferax* group or a *Pseudomonas* group.

13. The method for manufacturing the negative electrode according to claim 11, wherein said metal-reducing bacteria contain *Shewanella loihica* or *Shewanella oneidensis*.

14. The method for manufacturing the negative electrode according to claim 10, wherein said conductive fine particles comprise $\alpha$-$Fe_2O_3$, $\alpha$-FeOOH, $\gamma$-$Fe_2O_3$, $\epsilon$-$Fe_2O_3$, $Fe_3O_4$ or ferric sulfide.

15. The method for manufacturing the negative electrode according to claim 14, wherein said microorganisms are metal-reducing bacteria.

16. The method for manufacturing the negative electrode according to claim 15, wherein said metal-reducing bacteria include bacteria of a *Shewanella* group, a *Geobacter* group, a *Rhodoferax* group or a *Pseudomonas* group.

17. The method for manufacturing the negative electrode according to claim 15, wherein said metal-reducing bacteria contain *Shewanella loihica* or *Shewanella oneidensis*.

\* \* \* \* \*